US00PP25341P3

(12) United States Plant Patent
Fredette

(10) Patent No.: US PP25,341 P3
(45) Date of Patent: Mar. 10, 2015

(54) ***PETUNIA* PLANT NAMED 'DASAJA1'**

(50) Latin Name: ***Petunia* sp.**
Varietal Denomination: DaSaJa1

(75) Inventor: Jeffrey R. Fredette, Otisville, MI (US)

(73) Assignee: Jeffrey R. Fredette, Otisville, MI (US)

( * ) Notice: Subject to any disclaimer, the term of this patent is extended or adjusted under 35 U.S.C. 154(b) by 72 days.

(21) Appl. No.: 13/506,541

(22) Filed: Apr. 26, 2012

(65) Prior Publication Data

US 2013/0291264 P1 Oct. 31, 2013

(51) Int. Cl.
*A01H 5/00* (2006.01)

(52) U.S. Cl.
USPC ..... Plt./356.13

(58) Field of Classification Search
CPC ..... A01H 5/02
USPC ..... Plt./356.13, 356.23
See application file for complete search history.

(56) References Cited

U.S. PATENT DOCUMENTS

PP10,278 P 3/1998 Murakami
PP21,649 P2 * 1/2011 Heiser ..... Plt./356.13

* cited by examiner

*Primary Examiner* — June Hwu
(74) *Attorney, Agent, or Firm* — Gifford, Krass, Sprinkle, Anderson & Citkowski, P.C.

(57) ABSTRACT

A new and distinct variety of *petunia* plant as characterized by its distinctive flower color and its dark green foliage.

4 Drawing Sheets

Latin name: *Petunia* sp.
Varietal denomination: 'DaSaJa1'.

FIELD OF THE INVENTION

The invention is directed to a new variety of a *petunia* plant and more particularly to a *petunia* plant that has a growth habit and produces a flower of a color different than present *petunia* plants.

BACKGROUND OF THE INVENTION

The invention herein is a new and distinct variety of *Petunia* sp. The new *Petunia* is botanically known as 'DaSaJa1'. I discovered the 'DaSaJa1' *Petunia* in a cultivated area on my farm in Otisville, Mich., in March 2010.

The 'DaSaJa1' *Petunia*, was a naturally occurring whole plant mutation. The 'DaSaJa1' *Petunia* began to exhibit qualities distinctly different from other types of *petunias* in the surrounding area, namely, the other *petunias* in the surrounding area had flowers that are solid red in color, and generally upright in their growth, and thus taller than the 'DaSaJa1' *Petunia*. Further the foliage of the other *petunias* in the area exhibited a lighter shade of green, and the petal margins were solid red.

The 'DaSaJa1' *Petunia* is unlike other *petunia* plants in terms of both its flower color and its growth habit. The 'DaSaJa1' *Petunia* exhibits a limited growth in height, and spreads outwardly clinging to its surrounding areas. As shown in FIG. 3, when potted in suspension, the overall shape of the 'DaSaJa1' *Petunia* is generally spherical, and the internodes grow upright to a limited height so as to remain rigid. A rigid internode is atypical of *Petunias* which have internodes that grow upright and then bend due to the weight of the flower or leaves. Another example of a related known cultivar in which the 'DaSaJa1' *Petunia* is different from is a *petunia* plant named 'Bhtun31501' (U.S. Plant Pat. No. 21,649) also known as "Pretty Much Picasso." Bhtun31501 has dark purple with green colored margin flowers while 'DaSaJa1' *Petunia* has red with thin green margin flowers.

Asexual reproduction of the 'DaSaJa1' *Petunia* began on or about May 2010 by vegetative cuttings. Since May 2010 several vegetative cuttings were performed at approximately 60 day to 90 day intervals in Otisville Mich.

SUMMARY OF THE INVENTION

'DaSaJa1' is a distinctive, new variety of a *Petunia* plant sp characterized by its flower which is a red to pink shade color streaking from the top of the throat to the petal margin, its dark green foliage and the short length of its upright internodes. These traits are maintained when propagated asexually.

DETAILED DESCRIPTION OF THE PREFERRED EMBODIMENT

Figure 1:
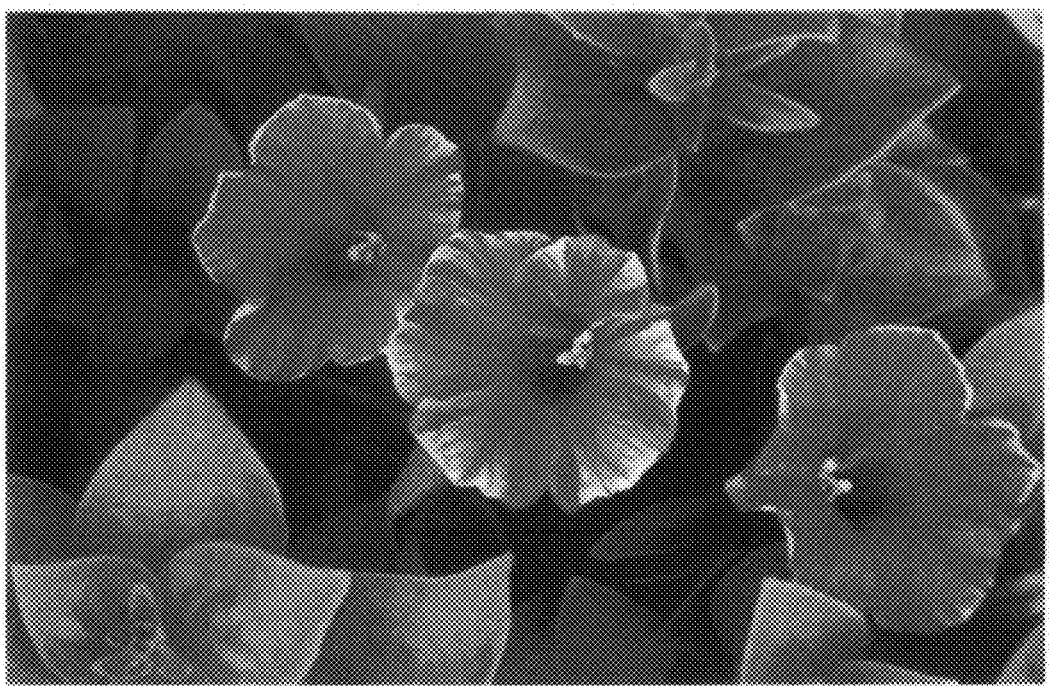
FIGS. 1 and 2 are close up photographs of the flowers and the foliage of the *petunia* plant of the present invention.
Figure 2:
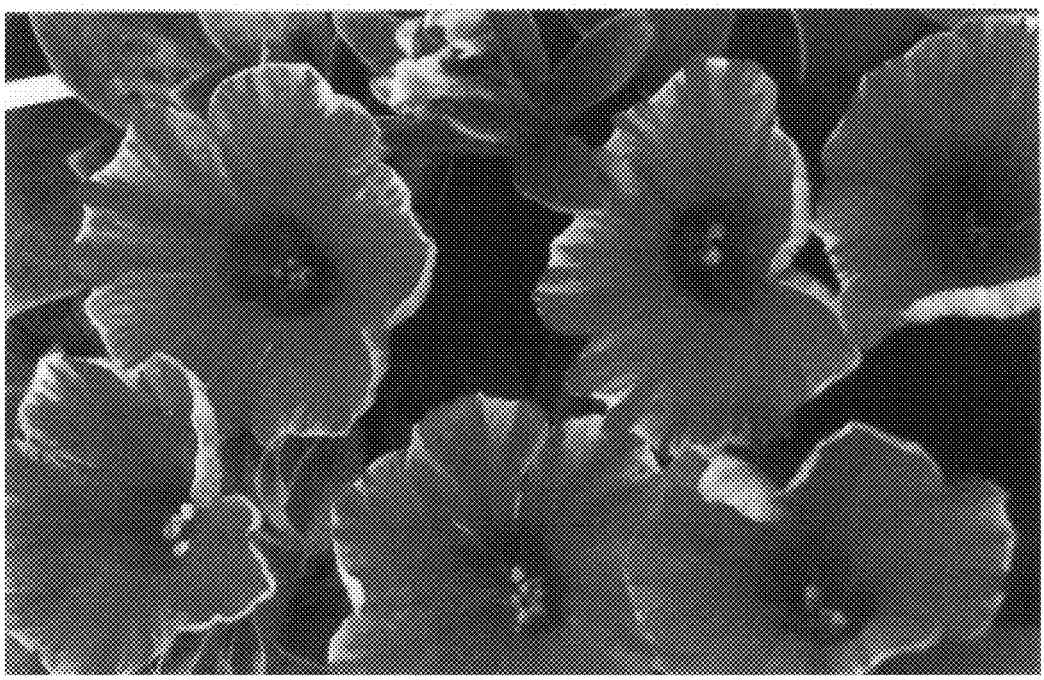
Figure 3:
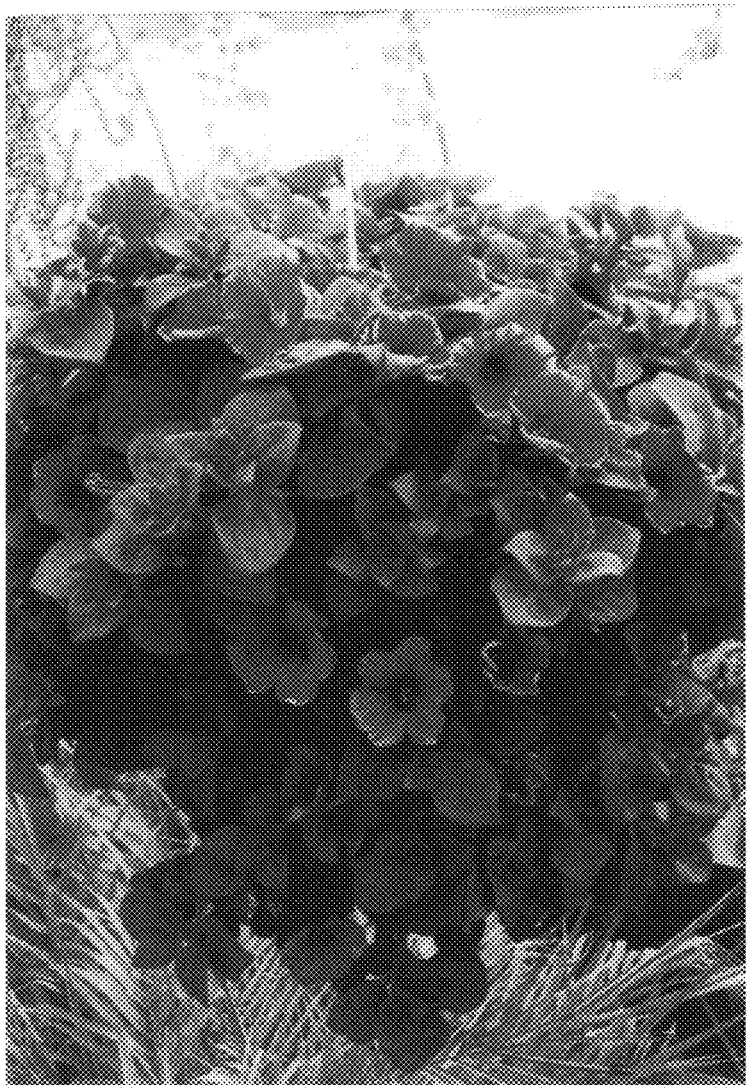
FIGS. 3 and 4 show the overall appearance of the 'DaSaJa1' *petunia* plant of the present invention.
Figure 4:
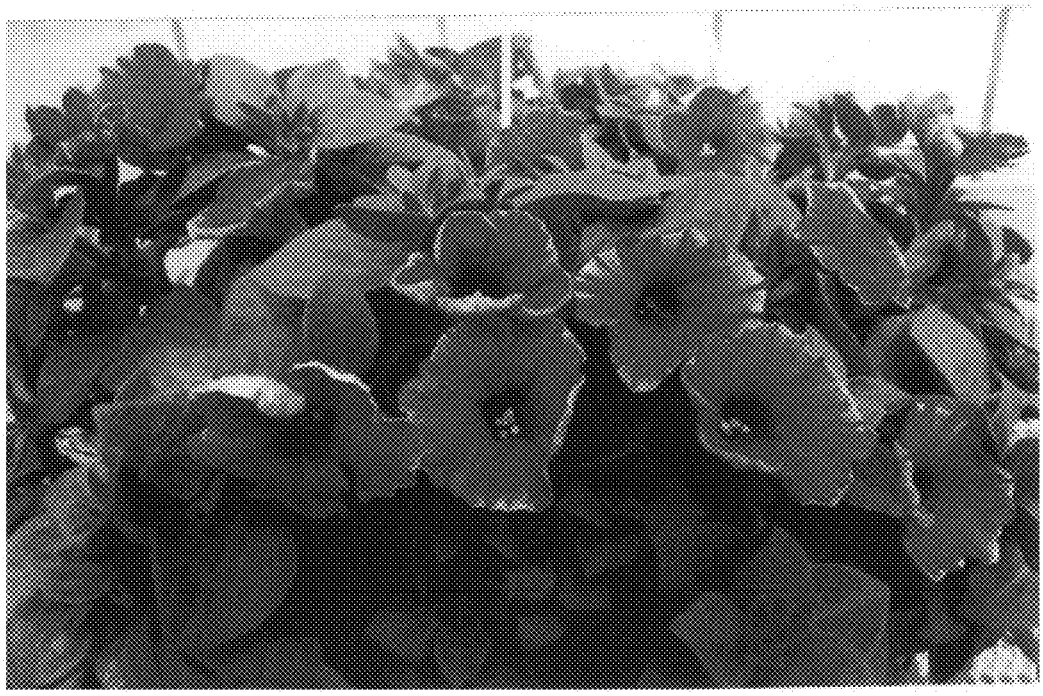

The invention was discovered, reproduced and observed by the Applicant in Otisville, Mich. beginning in March, 2010. Asexual reproductions of the 'DaSaJa1' *Petunia* by vegetative cuttings, since May 2010, show the unique features of the 'DaSaJa1' *Petunia* to be stable and true to type in successive cuttings. The unique characteristics of the 'DaJaSa1' *Petunia* include picotee type flowers with red to pink shades streaking throughout, the flower further includes a thin green edge. The 'DaSaJa1' *Petunia* is further distinguishable from other *Petu-*

*nias* in its thick dark green foliage. The 'DaSaJa1' *Petunia* is freely branching and includes an outwardly spreading/trailing habit. The description is provided utilizing The R.H.S. Colour Chart 2001.

The height of the 'DaSaJa1' *Petunia* is approximately 13 cm and flowers year around in moderate climate with a flower response which is indifferent to day length. The propagation is by vegetative cuttings with rooting by roots from the cutting base. Root initiation takes 7 to 10 days.

The 'DaSaJa1' *Petunia* has a plant spread averaging between 91 to 121 cm. The spread is measured by the longest distance between opposing peripheral edges of the plant. The measurement is also based upon a potted plant grown in a controlled climate. The 'DaSaJa1' *Petunia* an annual flowering plant. Its growth habit is outwardly spreading and trailing. It is a freely branching with approximately 14 lateral branches and numerous secondary and tertiary branches per plant.

The foliage includes a plurality of leaves each having a general elliptic shape wherein the outer edge is pointed with a tendency of point downwardly with respect to an upper surface of the leaf. The average leaf length is 6 cm for a mature leaf and a width of 3.8 cm and has a pubescent texture on both leaf surfaces. The color of the upper surface of the leaf is close to RHS 143A. The stem is strong and freely branching with a length of 30 to 50 cm and a diameter of 0.5 to 0.8 cm with a pubescent texture on both the upper and lower surfaces. The stem has an average internode length of 0.8 cm. Lateral branch has a length of about 53 cm. The texture of both the upper and lower surfaces of the petiole is pubescent. The color of the petiole is close to 146B.

The flower is a single type facing upward to horizontal, funnel shaped with a flower bud length of 4 cm and a width of 1 cm. The color of the flower is a red to pink shade streaking from top of the throat to petal margin.

Flower type and habit: (1) single salverform flowers; (2) flowers face outward and upward; and (3) freely flowering habit.

Flowering season: (1) day length neutral; (2) long flowering period; and (3) blooms year round in moderate climate.

Flower size: (1) Diameter is about 4.5 cm; (2) Depth is about 4.5 cm; and (3) Tube length is about 2.7 cm.

Flower buds: (1) Length is about 4 cm; and (2) width is about 1 cm.

Quantity/arrangement of the petals is generally five petals fused in a single whorl with a funnel form. The petal lobe length from throat is about 2 cm.

Petal lobe width is about 2 cm. Petal lobe margin is jagged and slightly upcurved. The upper surface of the petal lobe has a texture that is smooth with minute pubescence along margins. The lower surface of the petal lobe has a texture that is pubescent. The texture of the throat is smooth. The texture of the tube is pubescent along the entire surface. The petal color is lateral red to a pink shade streaking from top of throat to petal margin, including colors close to RHS 44A, 49C, 50D, 54D, 55C; margin, close to 149A; venation, close to 44A; throat, close to 43A.

The 'DaSaJa1' *Petunia* has a plurality of single whorls, each whorl having five (5) sepals. The shape of an individual sepal is generally subulate; with a length of approximately 2.7 cm, and a width of about 1 cm. The sepals have a pubescent texture on both surfaces. The color of the upper surface of the sepal is close to 141C. The color of the lower surface of the sepal is close to 141D. The peduncle has a length of about 2 cm, and a width of about 2 mm. The texture of the peduncle is pubescent on all surfaces. The color of the peduncle is close to 141D.

Reproductive organs. There are approximately five (5) stamens per flower. The filament length is about 1.3 cm. Filament color is green white close to 157D. The anther shape is generally oval and the anther length is about 2 mm. The pollen color is close to 160C. There is one pistil per flower. The pistil length is about 2 cm. The shape of the stigma is generally oval, and the stigma width is about 3 mm. The stigma color is close to 142A. The style color is close to 150B.

The seed and/or fruit production has not been observed.

Pathogen/pest resistance: Plants of the 'DaSaJa1' *Petunia* have been noted to be resistant to pathogens common to *Petunia*. However, resistance to pests common to *Petunia* has not been observed.

Garden performance: Plants of the 'DaSaJa1' *Petunia* have been observed to have good garden performance and have been observed to tolerate rain, wind and temperatures ranging from about 0° C. to about 40° C.

It should be apparent to one with ordinary skill in the art that I have described a new and distinct variety of a *petunia* plant, 'DaSaJa1', characterized by dark green foliage, and a flower having red to pink shades streaking throughout, and a thin green edge.

Having now described the new and distinct variety of *petunia* plant which I have discovered and asexually produced, I claim:

1. A new and distinct variety of *petunia* plant, substantially as herein illustrated and described, characterized by its distinctive flower colors and its dark green foliage.

* * * * *